United States Patent [19]

Eibl et al.

[11] Patent Number: 5,415,248

[45] Date of Patent: May 16, 1995

[54] APPARATUS FOR CLEANING DENTAL TOOLS

[75] Inventors: Johann Eibl, Schwarzgraben; Peter Malata, Jr., Hödlwaldgasse, both of Austria

[73] Assignee: Dentalwerk Bürmoos Gesellschaft m.b.H., Bürmoos, Austria

[21] Appl. No.: 96,018

[22] Filed: Jul. 22, 1993

[30] Foreign Application Priority Data

Jul. 22, 1992 [AT] Austria .................................. 1500/92

[51] Int. Cl.[6] .............................................. F01M 9/00
[52] U.S. Cl. .................. 184/6.11; 184/55.1; 433/104
[58] Field of Search ............ 184/6.11, 7.4, 55.1; 433/104; 415/904

[56] References Cited

U.S. PATENT DOCUMENTS

| | | | |
|---|---|---|---|
| 4,403,958 | 9/1983 | Löhn | 433/126 |
| 4,486,174 | 12/1984 | Eibofner et al. | 433/104 |
| 4,486,175 | 12/1984 | Fisher et al. | 433/104 |
| 4,544,355 | 10/1985 | Eibofner et al. | 433/104 |
| 4,902,226 | 2/1990 | Elliott et al. | 433/104 |
| 4,990,087 | 2/1991 | De Rocchis et al. | 433/104 |
| 5,096,421 | 3/1992 | Seney | 433/82 |
| 5,165,503 | 11/1992 | Hoffman | 184/55.1 |

FOREIGN PATENT DOCUMENTS 646509 10/1962 Italy .................................... 184/55.1

Primary Examiner—Thomas E. Denion
Attorney, Agent, or Firm—Friedrich Kueffner

[57] ABSTRACT

An apparatus for cleaning dental tools includes an instrument connection for blowing oil and/or cleaning agent, possibly in the form of a spray mist, through the instruments and subsequently drying the instruments with compressed air. A drive unit for driving movable instrument components may additionally be provided. The control of the various cleaning phases and of the conveyance of the cleaning liquids takes place pneumatically. In particular, a short-term flow of compressed air displaces at least one piston against a spring which causes oil and/or cleaning agent to be pressed into the instrument. A control edge of the piston produces a connection between the compressed air supply and the instrument connection when the piston leaves its upper position of rest. When the piston travels back in the opposite direction under the force of the spring after the short-term flow of compressed air has ended, the supply of oil and/or cleaning agent to the instrument connection is interrupted, while the supply of compressed air is maintained until the piston has again reached its upper position of rest.

10 Claims, 3 Drawing Sheets

APPARATUS FOR CLEANING DENTAL TOOLS

BACKGROUND OF THE INVENTION

1. Field of the Invention

The present invention relates to an apparatus for cleaning dental hand tools.

2. Description of the Related Art

A variety of apparatus of the above-described type are commercially available. For example, an electrically driven device is sold by Dental Festin GmbH & Co. KG, Germany, under the name Rotosuc. This device pumps cleaning oil at increased pressure for half a second and subsequently air at a decreased pressure for approximately 20 seconds through the instruments. As a result, the cleaning oil is pressed into all hollow spaces, corners and gear parts of the instrument, impurities are flushed out and an oil film remains for providing lubrication in the bearings and between the gear wheels. The distribution of the cleaning oil in the instruments is further improved by rotating the hand pieces and angle pieces during the treatment, wherein, contrary to the normal operation, the internal components remain stationary and the outer components are rotated.

A device for cleaning, disinfecting and lubricating dental instruments is sold by Orochem Chemie AG, Switzerland, under the name Turbocid. The device operates by rinsing with cold water under pressure the slowly rotating instruments, so that all internal surfaces are cleaned and the instruments are washed out. Subsequently, any rinsing agent remaining in the instruments is blown out by means of compressed air. The slowly rotating instruments are then disinfected under pressure by means of a special disinfecting agent. Subsequently, the disinfecting agent is blown out. Finally, lubricating oil is introduced and any excess lubricating oil is also blown out. The outer surfaces of the instruments are also disinfected by spraying disinfecting agent thereon and the surfaces are then dried with compressed air. The various procedures described above are controlled electronically, and up to four instruments can be treated simultaneously.

EP-A2 0 300 945 discloses an apparatus in which dental instruments are rinsed out by several liquids, and air for drying and finally lubricating oil are blown into the instruments. During the treatment, the movable parts of the instrument are rotated in order to improve the cleaning effect. The liquids are pressed from containers to the instruments by means of compressed air, wherein the compressed air is supplied to the apparatus from outside. The flow of compressed air to the individual liquid containers or directly to the instruments is effected by means of electrically operated valves. The entire cycle is controlled electronically and the sequence thereof can be changed by the operator.

In the field of caring for dental instruments, manual devices have become known for individually cleaning an instrument. However, these devices are either cumbersome to operate or their possibilities of use are limited, so that they have not been successful on the market.

The above-described known stationary devices all have in common that they use an electronic circuit for controlling the cleaning sequence, wherein the electronic circuit actuates various solenoid valves or electrically operated valves. Accordingly, these devices are of complicated and cumbersome construction. In connection with electronic components, a particular problem is the fact that various liquids and electric current are located closely adjacent each other. In addition, there are problems concerning the adaptation of the devices to the regulations and standards of various countries, which means that the known stationary devices are expensive.

SUMMARY OF THE INVENTION

Therefore, it is the primary object of the present invention to provide an apparatus of the above-described type in which the disadvantages discussed above are avoided. In particular, an apparatus for cleaning dental instruments is to be provided which is robust, simple and intrinsically safe and still can carry out the same cleaning procedures as the known devices.

In accordance with the present invention, the control or regulation of the various cleaning phases and the transportation of the cleaning liquids is carried out pneumatically.

Preferably, the compressed air required for operating the apparatus is supplied from a dental treatment chair. The pneumatic control can be effected by means of pneumatic valves which, after receiving a pressure pulse, release a line for a predetermined, and possibly adjustable, period of time. The transportation of liquid can be effected, for example, by means of pneumatically operated pumps or by means of spring-biased pistons, as described in more detail below.

A further development of the present invention provides that compressed air supplied from an external or internal source is admitted through a manually operated valve to a piston of a regulating unit and the compressed air presses the piston against the force of a spring until the piston reaches a stop (lower dead center). As a result of this displacement of the piston, a predetermined amount of oil and/or cleaning agent is forced from reservoirs through lines to at least one connection point for at least one instrument and, after being mixed with compressed air, into the instruments. Control edges of the piston connect the compressed air source to a compressed air line which leads to the connection point as long as the piston is not in its initial position (upper dead center).

When the supply of compressed air to the regulating unit is terminated, the piston is moved by means of the spring back into its initial position. The compressed air additionally drives a turbine of the apparatus which, in turn, is mechanically connected to a drive member for the movable parts of the instrument to be cleaned, so that the movable parts of the instrument are actually moved during the time oil is blown into the instrument. The cleaning liquid is forced into the fluid-conducting ducts of the instrument.

Branching off from the air supply following the control edge of the piston toward the turbine in the region of the connection point is a line each which is connected to the respective connection opening of the instrument and is in communication with the respective line for the oil or cleaning agent. In this manner, the instrument, to the extent that it has movable parts, is moved and during the beginning of the cleaning phase, an oil spray mist or cleaning agent spray mist is formed by the compressed air and is blown through the respective hollow spaces. After the piston reaches the lower dead center, oil or cleaning agent are no longer supplied, so that the spray mist is automatically replaced by pure compressed air and the device is blown dry. When cleaning manual dental turbines whose movable parts are placed in motion by compressed air and not by mechanical couplings (turbines), an adaptor is placed on the holding device of the apparatus, so that the compressed air arriving from the apparatus turbine is introduced into the turbine hand piece and results in a rotation of the hand piece turbine and, thus, an improved cleaning action.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENT

Figure 1A:
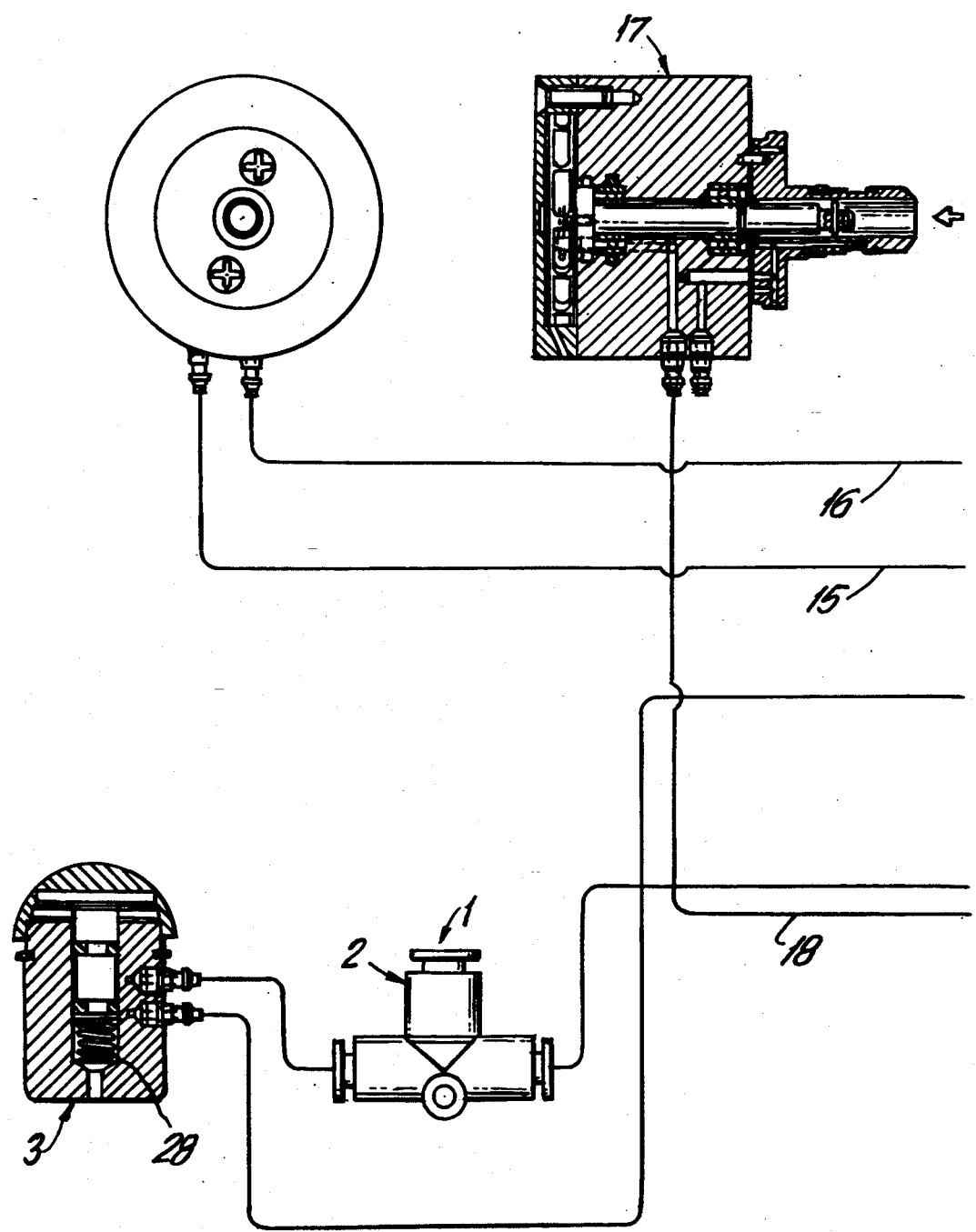
FIGS. 1a and 1b each constitute half of a pneumatic or hydraulic diagram of an embodiment of the apparatus according to the present invention, wherein individual structural components are shown in detail in sectional views.
Figure 1B:
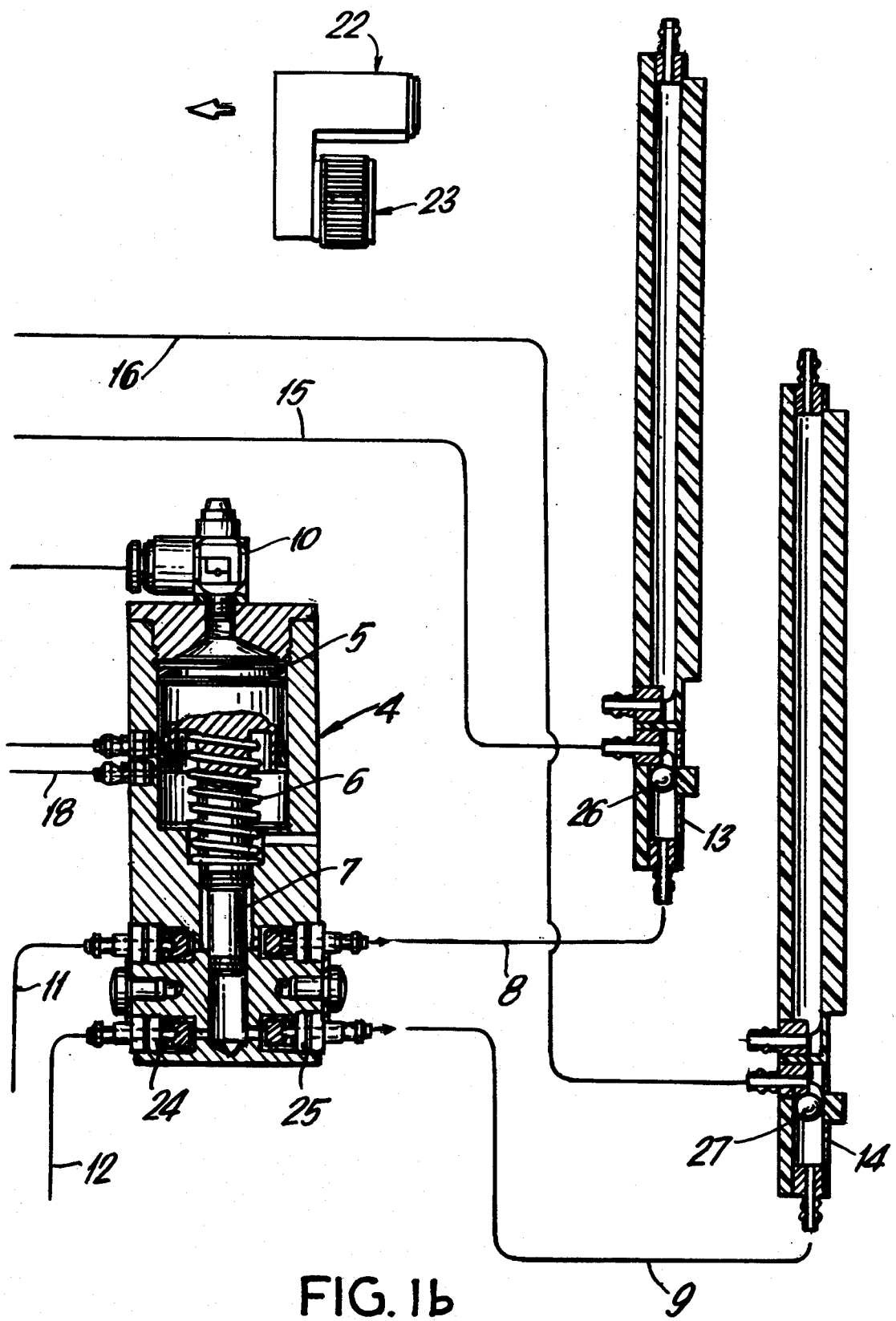

As illustrated in FIGS. 1a and 1b of the drawing, external compressed air is supplied to the apparatus at 1 and reaches a tee 2 in which a pressure reduction and/or a purification by means of an inserted filter may be carried out. The compressed air reaches from the tee 2 through a line to an actuating button 3 which starts the cleaning procedure when being pressed down.

When the button 3 is pressed downwardly against the force of a spring 28, the supply of compressed air and the continuing line are connected to each other for a relatively short time, so that compressed air is conducted from the tee 2 through the actuating button 3 to the head 10 of a regulating unit 4.

A piston 5 is provided in the interior of the regulating unit 4. A spring 6 presses the piston 5 upwardly against the head 10 of the regulating unit 4. When compressed air is admitted to the regulating unit 4, the piston 5 is pressed downwardly against the force of the spring 6, and the piston rod 7, constructed as a double piston, presses oil into the line 8 and cleaning agent into the line 9. A return flow of the two fluids into the lines 11 and 12 is prevented by check valves 24 and 25 in the cleaning agent line 9 and by two analogous check valves, not provided with reference numerals, in the oil line 8.

After the actuating button 3 has been released, the spring 28 in the actuating member presses the actuating button 3 together with a piston again upwardly, so that the supply of compressed air to the head 10 of the regulating unit 4 is interrupted. The force of the spring 6 presses the piston 5 upwardly, so that a ventilation is provided in the head 10 which limits the speed of the piston 5.

In one possible embodiment, the ventilation is connected directly to the outside. In this case, the ventilation is open even during the supply of compressed air. However, the amount of air flowing out is so small that it does not impair the movement of the piston against the spring 6.

In the illustrated embodiment, the ventilation is provided between the head 10 of the regulating unit 4 and the supply of compressed air from the actuating button 3, so that ventilation takes place through a bore in which the spring 28 is mounted.

As the piston 5 now moves upwardly, the two piston portions of the piston rod 7 withdraw oil from the line 11 and cleaning agent from the line 12 from respective containers, wherein the check valves 24, 25 in the cleaning agent line 9, 12 and the two check valves, not identified by reference numerals, in the oil line 8, 11 ensure together with the spaces in the regulating unit for the piston rod 7 that the directions of movement of the oil and of the cleaning agent are maintained.

The oil and the cleaning agent are conducted to the instrument connection 17 through display units 13, 14 and continuing lines 15, 16. In addition, compressed air is supplied to the instrument connection 17 from the tee 2 through the regulating unit 4 and the supply line 18.

A control surface of the piston 5 in the regulating unit 4 ensures that compressed air is always supplied to the line 18 from the tee 2 when the piston 5 is removed from its position of rest in the dead center at the side of the head.

Figure 2:
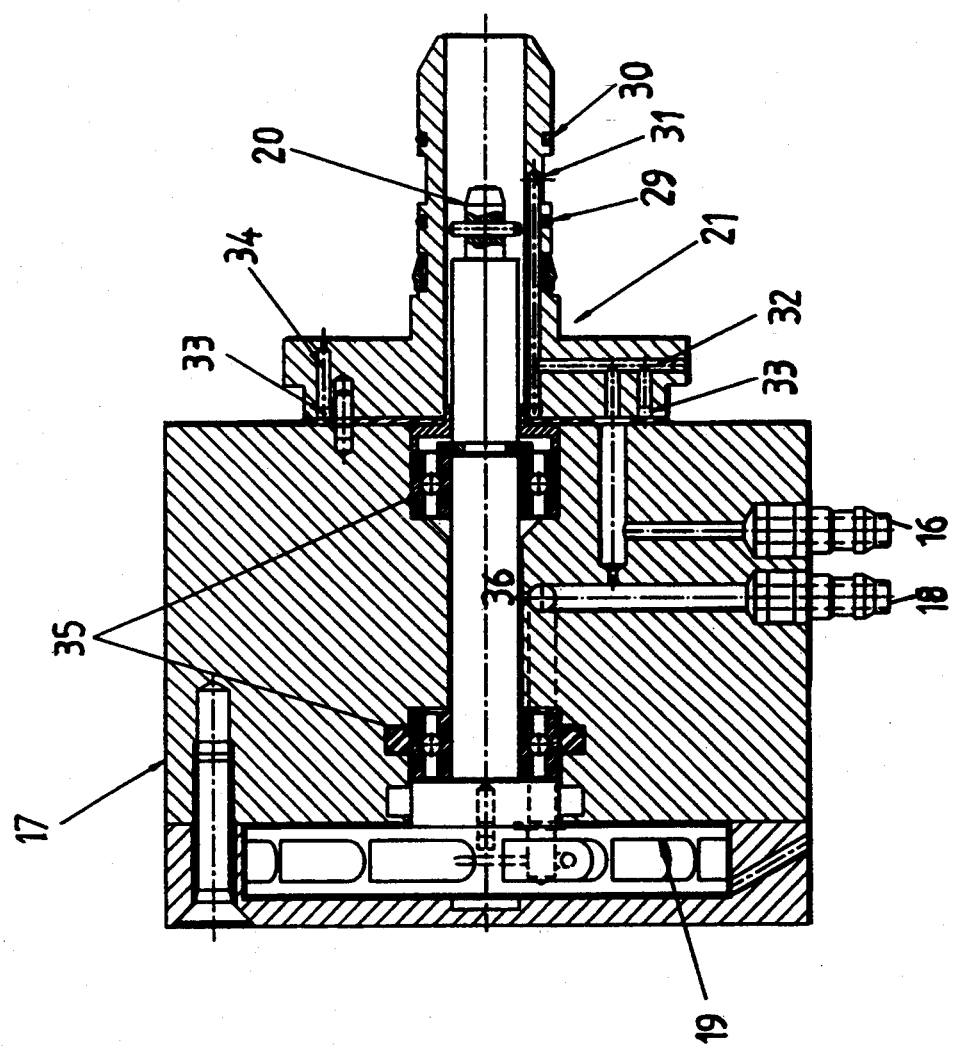
FIG. 2 is a sectional view, on a larger scale, of the instrument connection.

As more clearly illustrated in FIG. 2, the compressed air line 18 branches in the instrument connection 17 and drives through one of the line branches a turbine 19 which is mounted on a shaft whose end 20 on the side of the instrument is provided with a standardized drive member for dental instruments.

Either through this drive air which flows through the bearings of the shaft, or preferably through another branch from the compressed air line 18 not shown in FIG. 2, the interior of the dental instrument which contains the movable parts is supplied with an oil spray mist which is produced by the communication of the oil line 15 with a corresponding branch of the compressed air line 18.

Similarly, by guiding a branch of the compressed air line 18 together with the cleaning agent line 16, a cleaning agent spray mist is formed. Through a branch 31 which in a standardized manner ends between O-rings 29, 30 of the instrument connection 17 at 31, the cleaning agent spray mist is conducted to all inlets of fluid ducts of a dental instrument, such as, cooling water, cooling air, return flow line, etc.

If a dental instrument is to be cleaned which has its own drive in the form of an air turbine, an adaptor 22 is slid onto the instrument connection 17, wherein the adaptor 22 is provided with a receiving means for turbines at 23. The compressed air containing an oil mist drives the turbine in the handpiece, so that this turbine is also moved during the cleaning process.

In the illustrated embodiment, filling level indicators are integrally connected to sight glasses 13, 14 through which by movement of the balls 26, 27 the flow of the oil and cleaning agent, respectively, are indicated. Thus, the operator can determine with a single glance whether the apparatus is supplied with sufficient cleaning agent and oil.

A particular feature which makes it possible to clean a hand tool also from the outside is illustrated in FIG. 2. A secondary line 32 is branched off from the line which conducts the cleaning agent spray mist to the outlet 31. This secondary line 32 leads to an annular duct 33 which extends concentrically to the shaft of the turbine 19. Bores 34 extend at regular intervals from the annular duct to the end face of the instrument connection and form nozzles at the end face from which the cleaning agent spray mist is sprayed against the outside of the instrument.

In order to prevent oil-containing or contaminated air from reaching the area of the bearings 35 of the shaft, a connection 36 is provided between the compressed air supply 18 and the annular gap of the shaft between the bearings 35. Of course, this type of seal can only be used if air arriving from the turbine 19 is not conducted into the interior of the instrument.

The present invention is not limited to the embodiment described above and illustrated in the drawing. Rather, various modifications are possible.

For example, as mentioned above, the control can be effected by means of time switch valves, wherein the cleaning agent and/or oil can also be conveyed by applying pressure to the supply containers. Similar the illustrated embodiment, a compressed air pulse from the switch 3 would be conducted to at least one time switch valve.

In a preferred modification, three time switch valves connected in parallel are used, wherein two time switch valves effect the conveyance of the liquids and the third time switch valve, with a longer opening period, controls the supply of the compressed air to the hand tool. This makes possible an individually easily adjustable and changeable cleaning sequence.

In all modifications of the invention, the compressed air can also be supplied by a compressor provided in the apparatus without resulting in the above-discussed disadvantages because these devices are substantially more robust than the electronic control circuits.

It is also possible to provide several connection points for instruments or to use different cleaning agents for different fluid-conducting ducts of the instruments. In the illustrated embodiment, this can be easily achieved by a further modification of the piston rod 7.

It is also possible to make the cross sectional area of the blow opening at the head 10 of the regulating unit 4 adjustable, e.g., by a needle valve, in order to be able to deal with different degrees of contamination.

It is also not necessary that three pistons are mounted on a piston rod, however, this embodiment is particularly robust and space-saving. Different control characteristics can be realized for the individual fluids if several separate pistons with control edges are used.

The invention is not limited by the embodiments described above which are presented as examples only but can be modified in various ways within the scope of protection defined by the appended patent claims.

We claim:

1. A cleaning apparatus for dental instruments, the cleaning apparatus comprising an instrument connection for mounting a dental instrument thereon, the instrument connection comprising means for conveying at least one of oil and cleaning agent to the dental instrument and means for supplying compressed air to the dental instrument and pneumatic control means for regulating the means for conveying oil and cleaning agent to the dental instrument and the means for conveying compressed air to the dental instrument, further comprising a regulating unit comprising a piston movable in the regulating unit between an upper dead center position and lower dead center position, a spring for biasing the piston toward the upper dead center position, a compressed air line connecting the regulating unit with the instrument connection for applying a short-term flow of compressed air against the piston to move the piston against the spring from the upper dead center position to the lower dead center position, the piston having a control edge for effecting a connection between the compressed air line and the compressed air supply line when the piston is moved away from the upper dead center position, the piston further comprising means for supplying predetermined quantities of at least one of oil and cleaning agent from supply containers to the instrument connection, wherein the means for supplying oil and cleaning agent to the instrument connection is closed by the piston after the piston has reached the lower dead center position after the short-term flow of compressed air, while the compressed air line to the instrument connection remains open until the piston has again reached the upper dead center position.

2. The cleaning apparatus according to claim 1, further comprising a drive unit for driving movable instrument components.

3. The cleaning apparatus according to claim 2, wherein the instrument connection comprises a compressed air-operated turbine for driving the drive unit.

4. The cleaning apparatus according to claim 3, wherein for cleaning dental instruments with air turbines, an adaptor is connectable to the instrument connection for conducting air from the compressed air-operated turbine to an inlet line of the dental instrument.

5. The cleaning apparatus according to claim 1, wherein the regulating unit has a head, the head of the regulating unit defining a ventilation opening, the ventilation opening having a cross-sectional size, wherein the cross-sectional size of the ventilation opening determines the speed of the piston when the short-term flow of compressed air is applied.

6. The cleaning apparatus according to claim 5, comprising means for adjusting the cross-sectional size of the ventilation opening.

7. The cleaning apparatus according to claims 1, comprising an actuating unit including a piston movable against a spring for actuating the short-term flow of compressed air.

8. The cleaning apparatus according to claim 1, wherein the compressed air supply line is connected to a dental chair.

9. The cleaning apparatus according to claim 1, wherein the instrument connection further comprises a duct for conducting a cleaning agent spray mist, the instrument connection having an end face, a branch line connecting the duct with an annular duct and a plurality of nozzles provided in the end face.

10. The cleaning apparatus according to claim 1, wherein the instrument connection further comprises an annular space defined between bearings of a shaft, the compressed air-operated turbine being mounted on the shaft, the compressed air line connecting the regulating unit with the instrument connection being in communication with the annular space.

* * * * *